(12) United States Patent
Jackson (10) Patent No.: US 11,364,165 B2
(45) Date of Patent: Jun. 21, 2022

(54) MOTORIZED HOSPITAL BED ASSEMBLY

(71) Applicant: Deborah Jackson, Norwalk, CA (US)

(72) Inventor: Deborah Jackson, Norwalk, CA (US)

( * ) Notice: Subject to any disclaimer, the term of this patent is extended or adjusted under 35 U.S.C. 154(b) by 0 days.

(21) Appl. No.: 17/089,785

(22) Filed: Nov. 5, 2020

(65) Prior Publication Data

US 2022/0133561 A1    May 5, 2022

(51) Int. Cl.
*A61G 7/02*   (2006.01)
*A61G 7/05*   (2006.01)
*A61G 9/00*   (2006.01)

(52) U.S. Cl.
CPC .............. *A61G 7/02* (2013.01); *A61G 7/05* (2013.01); *A61G 9/003* (2013.01); *A61G 2200/327* (2013.01); *A61G 2203/12* (2013.01)

(58) Field of Classification Search
CPC . A61G 7/02; A61G 7/05; A61G 9/003; A61G 2203/12
See application file for complete search history.

(56) References Cited

U.S. PATENT DOCUMENTS

| 4,085,471 | A | 4/1978 | DiMatteo |
| D272,395 | S | 1/1984 | Sonder |
| 4,631,762 | A | 12/1986 | Fugett |
| 4,677,700 | A | 7/1987 | Su |
| 4,780,919 | A | 11/1988 | Harrison |
| 5,327,599 | A | 7/1994 | Bradley, Jr. |
| 5,926,875 | A | 7/1999 | Okamoto |
| 2006/0058587 | A1* | 3/2006 | Heimbrock .............. A61G 7/05 600/300 |
| 2008/0229502 | A1* | 9/2008 | Johnson ................... A61G 7/02 5/604 |

* cited by examiner

Primary Examiner — Fredrick C Conley (57) ABSTRACT

A motorized hospital bed assembly includes a bed frame that is positionable in an open position to define an opening in the bed frame. A motor is coupled to the bed frame and a drive unit is engaged to the motor. The drive unit urges the bed frame between the open position and the closed position. A toilet support is coupled to the bed frame and a portable toilet is positioned on the toilet support. The portable toilet is aligned with the opening when the bed frame is positioned in the open position to be employed by a patient while the patient is lying on the bed frame. A remote control is positionable on the bed frame and the remote control is in wireless communication with the drive unit to remotely control the drive unit.

9 Claims, 6 Drawing Sheets

MOTORIZED HOSPITAL BED ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to hospital bed devices and more particularly pertains to a new hospital bed device for facilitating a bed ridden patient to relieve themselves without assistance.

(2) Description of Related Art Including Information Disclosed Under 37 CFR 1.97 and 1.98

The prior art relates to hospital bed devices including a bed that includes a lifting portion for raising a patient's feet thereby facilitating the patient to employ a toilet located beneath the bed. The prior art discloses a variety of hospital beds that have a sliding portion that slides laterally to facilitate a patient to employ a bed pan that is positioned beneath the hospital bed. The prior art discloses a variety of hospital beds that have an opening permanently integrated therein, a toilet located beneath the opening and a means of covering the opening.

BRIEF SUMMARY OF THE INVENTION

An embodiment of the disclosure meets the needs presented above by generally comprising a bed frame that is positionable in an open position to define an opening in the bed frame. A motor is coupled to the bed frame and a drive unit is engaged to the motor. The drive unit urges the bed frame between the open position and the closed position. A toilet support is coupled to the bed frame and a portable toilet is positioned on the toilet support. The portable toilet is aligned with the opening when the bed frame is positioned in the open position to be employed by a patient while the patient is lying on the bed frame. A remote control is positionable on the bed frame and the remote control is in wireless communication with the drive unit to remotely control the drive unit.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
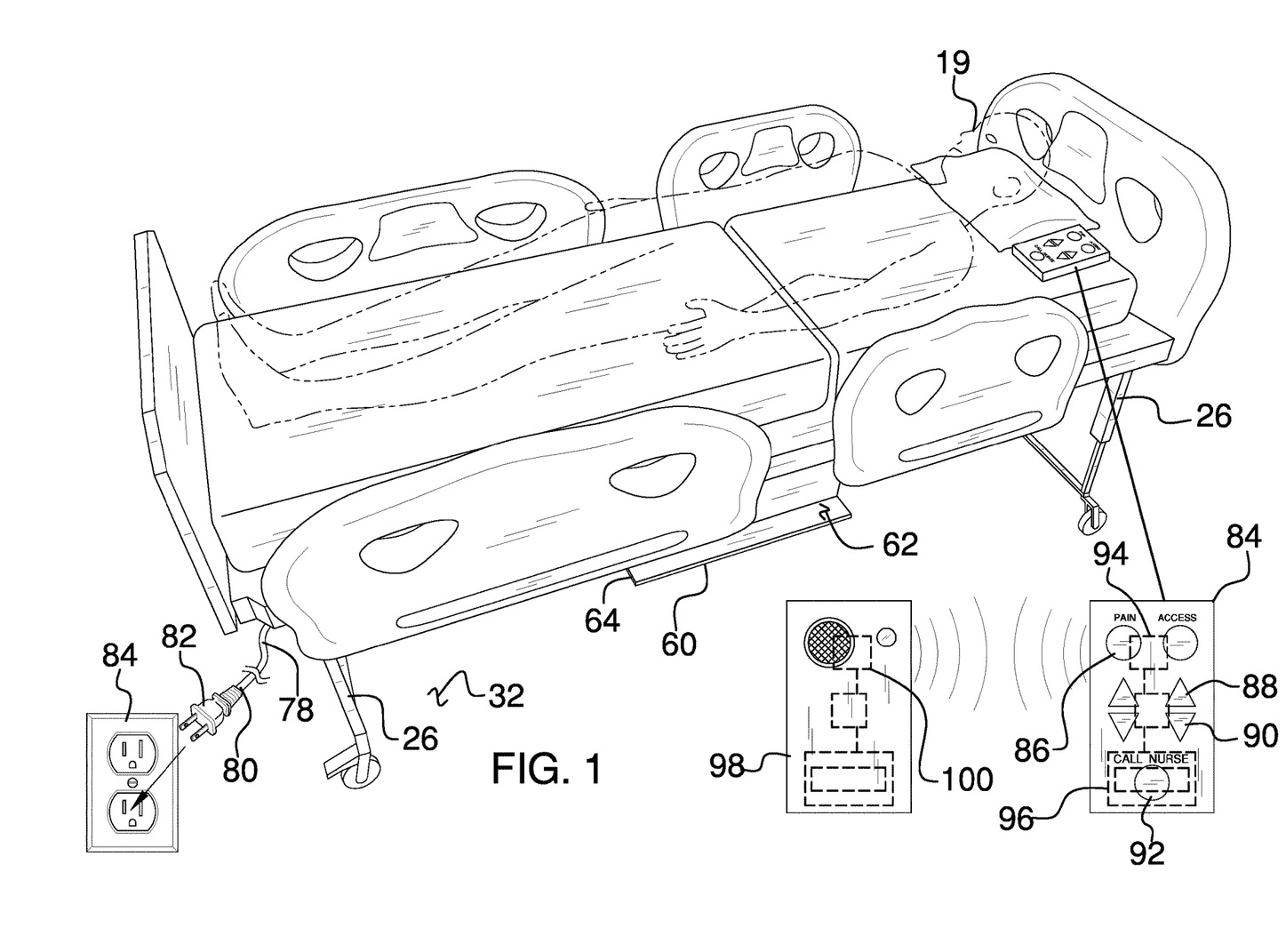
FIG. 1 is a top perspective view of a motorized hospital bed assembly according to an embodiment of the disclosure.
Figure 2:
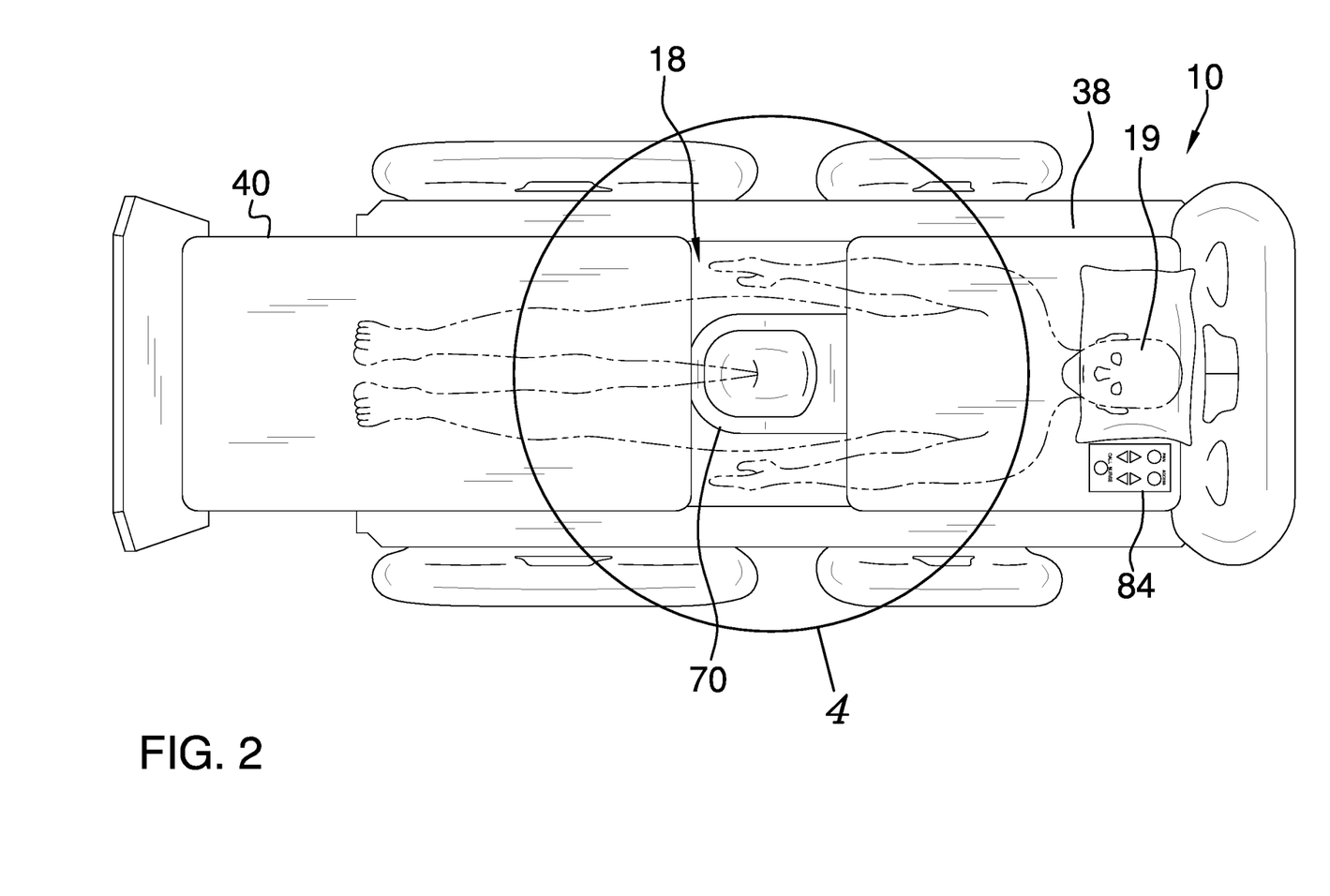
FIG. 2 is a top view of an embodiment of the disclosure showing a bed frame in an open position.
Figure 3:
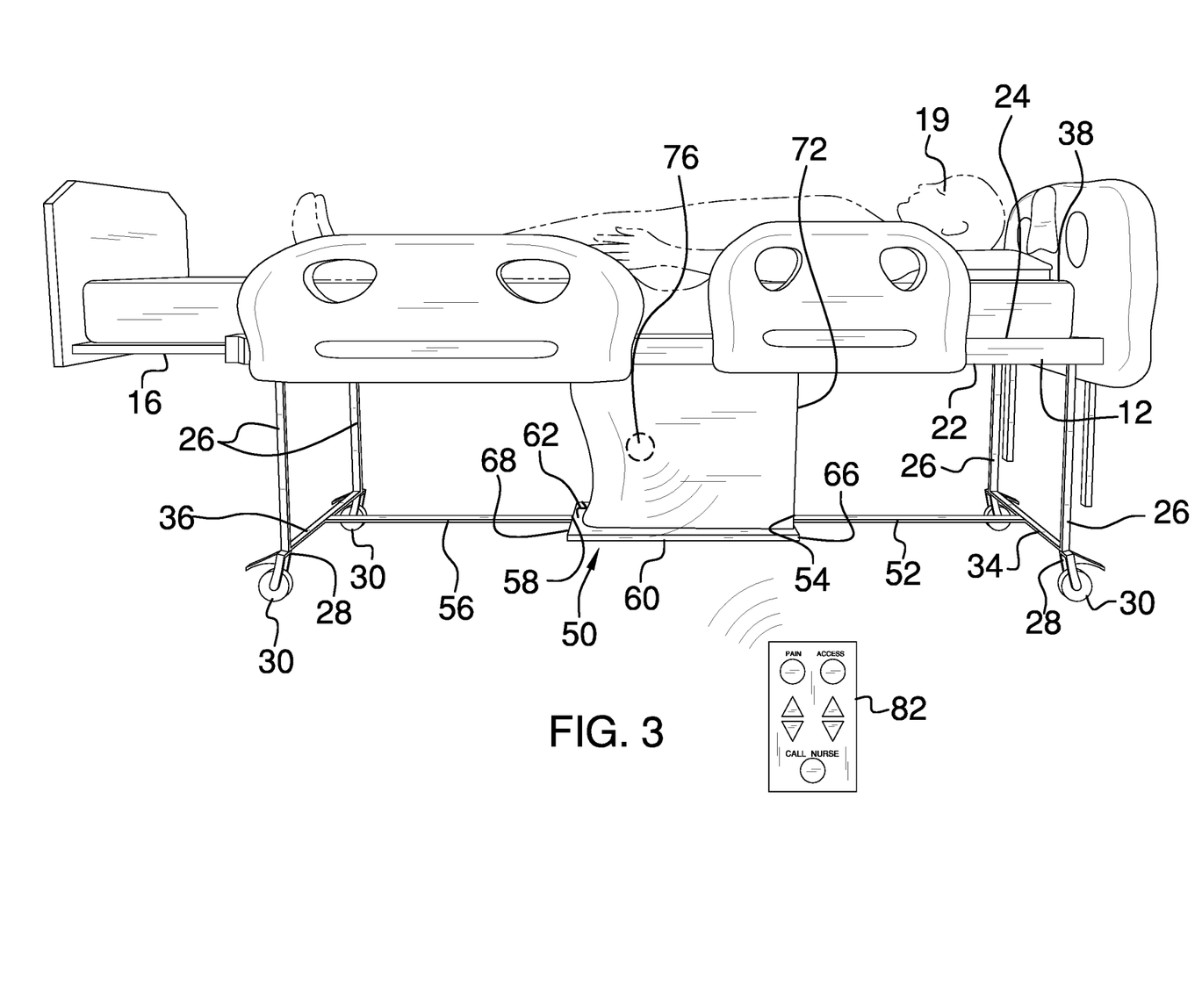
FIG. 3 is a left side view of an embodiment of the disclosure.
Figure 4:
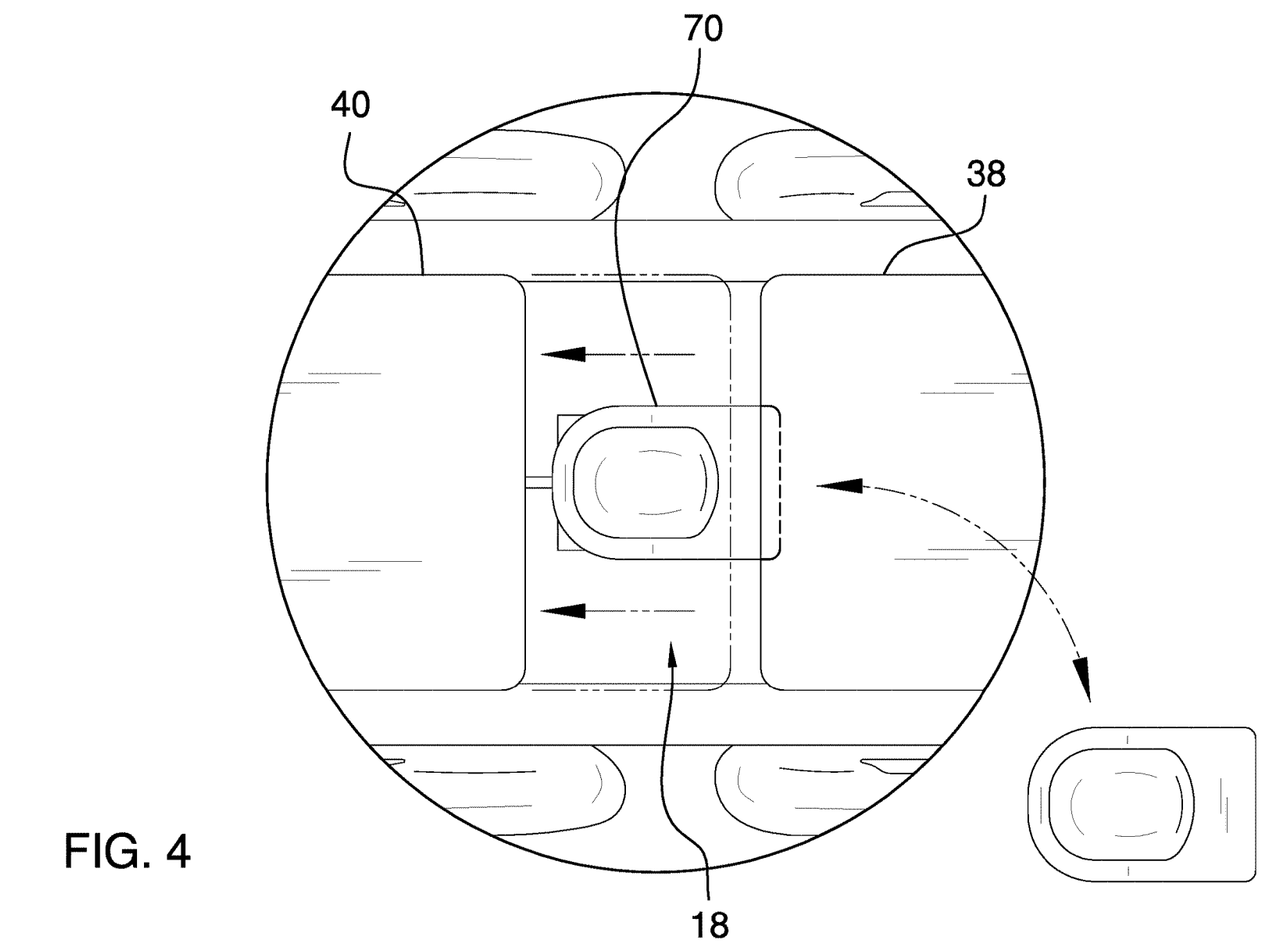
FIG. 4 is a detail view taken from circle 4 of FIG. 2 of an embodiment of the disclosure.
Figure 5:
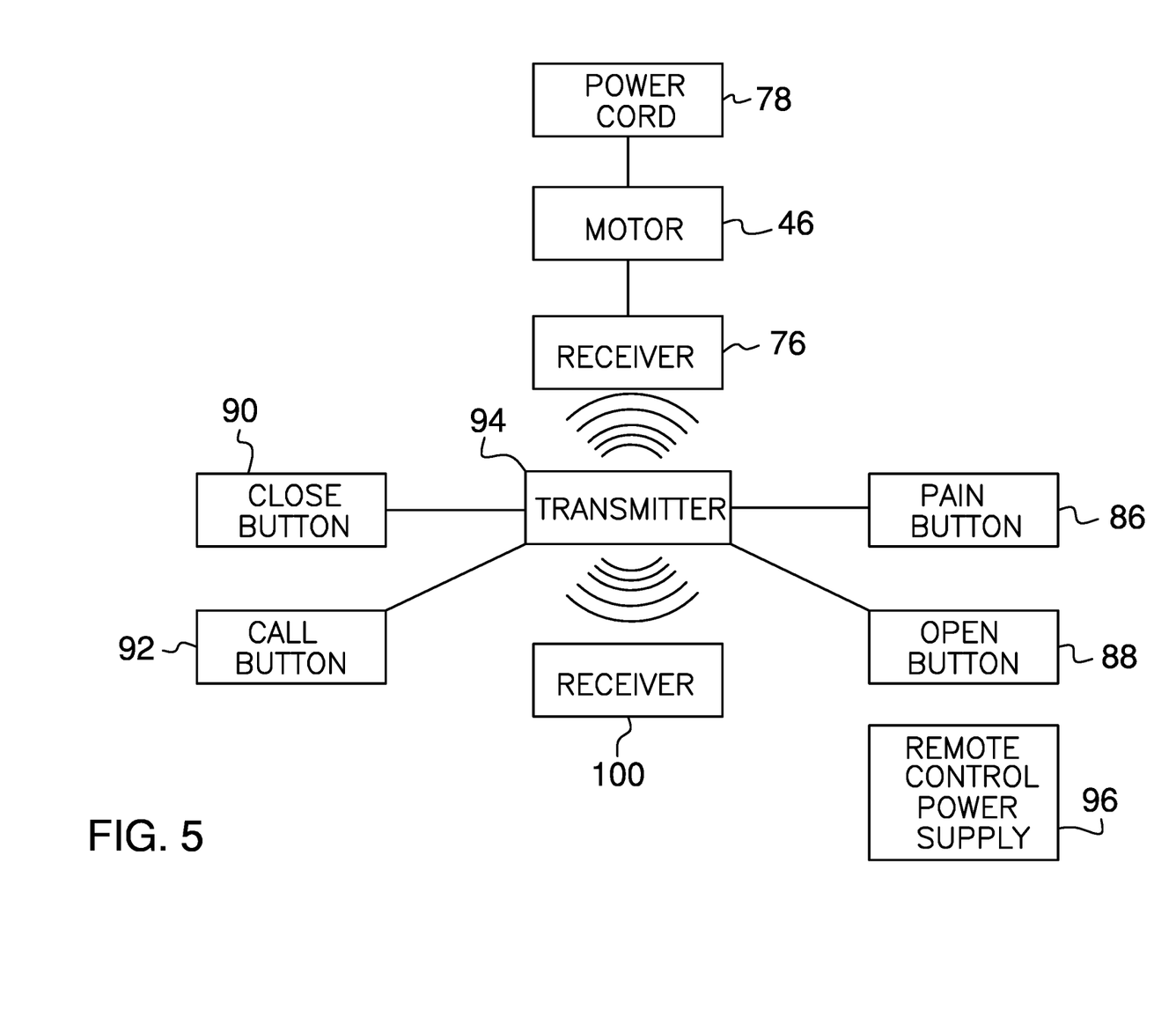
FIG. 5 is a schematic view of an embodiment of the disclosure.
Figure 6:
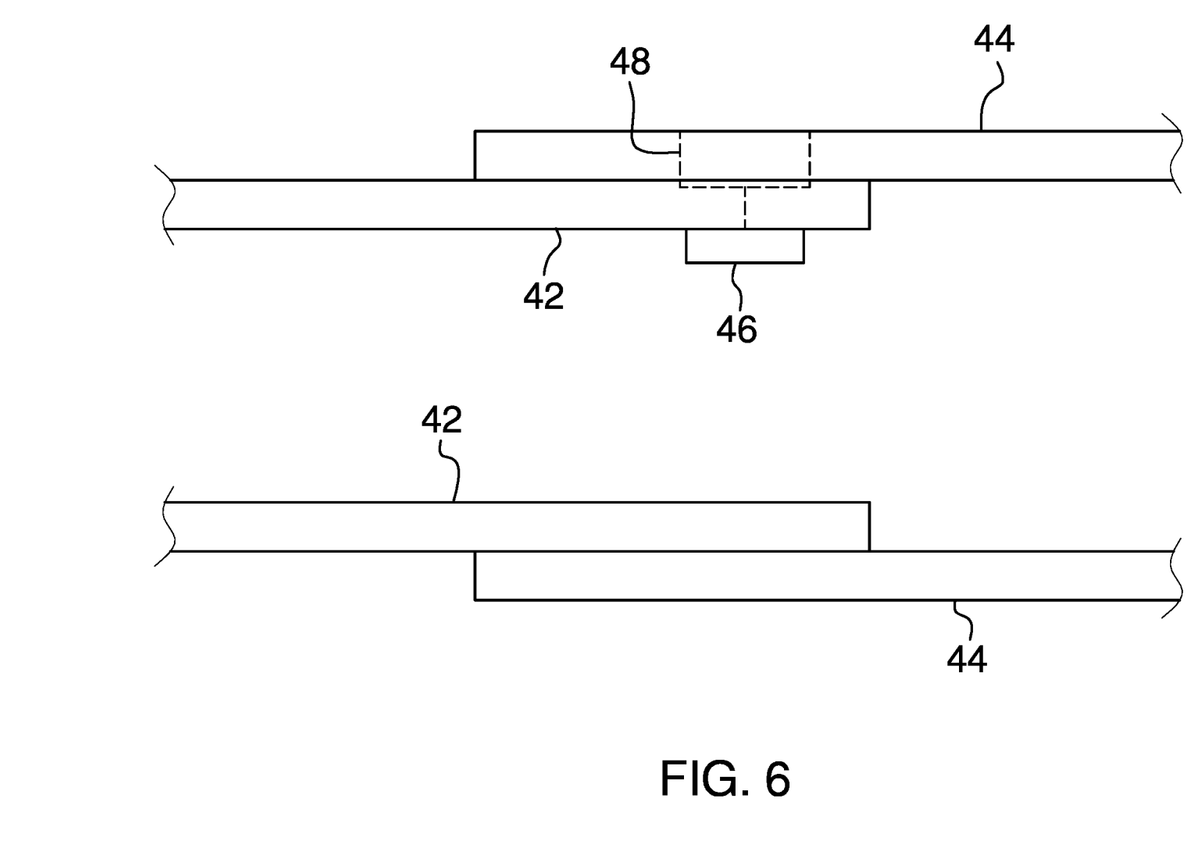
FIG. 6 is a top view of a pair of first rails, a pair of second rails, a motor and a drive unit of an embodiment of the disclosure.

With reference now to the drawings, and in particular to FIGS. 1 through 6 thereof, a new hospital bed device embodying the principles and concepts of an embodiment of the disclosure and generally designated by the reference numeral 10 will be described.

As best illustrated in FIGS. 1 through 6, the motorized hospital bed assembly 10 generally comprises a bed frame 12 that includes a first portion 14 slidably engaging a second portion 16. The bed frame 12 is positionable in a closed position having the first portion 14 abutting the second portion 16. Conversely, the bed frame 12 is positionable in an open position having the first portion 14 being spaced from the second portion 16 to define an opening 18 extending between the first portion 14 and the second portion 16. The first portion 14 has a length that is greater than a length of the second portion 16. In this way the opening 18 is aligned with a patient's 19 lower torso 20 when the bed frame 12 is positioned in the open position. Additionally, the bed frame 12 has a bottom side 22 and a top side 24.

A plurality of legs 26 is each coupled to and extends downwardly from the bed frame 12 and each of the legs 26 has a distal end 28 with respect to the bottom side 22 of the bed frame 12. A plurality of rollers 30 is each rotatably coupled to the distal end 28 of a respective one of the legs 26 to roll along a support surface 32 thereby supporting the bed frame 12 above the support surface 32. A first cross member 34 is coupled between a respective pair of the legs 26 that is associated with the first portion 14 of the bed frame 12. A second cross member 36 is coupled between a respective pair of the legs 26 that is associated with the second portion 16 of the bed frame 12.

A first mattress 38 is positioned on the first portion 14 of the bed frame 12 for having the patient 19 lie thereon and the first mattress 38 is positioned on the top side 24 of the bed frame 12. A second mattress 40 is positioned on the second portion 16 of the bed frame 12 for having the patient 19 lie thereon. The first mattress 38 abuts the second mattress 40 when the bed frame 12 is positioned in the closed position and the second mattress 40 is spaced from the first mattress 38 when the bed frame 12 is positioned in the open position. Additionally, the second mattress 40 is positioned on the top side 24 of the bed frame 12.

A pair of first rails 42 is provided and each of the first rails 42 is coupled to and extends away from the first portion 14 of the bed frame 12. Each of the first rails 42 is positioned on the bottom side 22 of the bed frame 12. A pair of second rails 44 is each of the second rails 44 is coupled to and extends away from the second portion 16 of the bed frame 12. Each of the second rails 44 is positioned on the bottom side 22 of the bed frame 12. Each of the second rails 44 slidably engages a respective one of the first rails 42 thereby slidably attaching the first portion 14 to the second portion 16.

A motor 46 is coupled to the bed frame 12 and the motor 46 rotates in a first direction or a second direction when the motor 46 is turned on. The motor 46 may comprise an electric motor or the like. A drive unit 48 is coupled to a respective one of the first rails 42 and the drive unit 48 engages the second rail 44 that engages the first rail 42 to which the drive unit 48 is coupled. The drive unit 48 is engaged to the motor 46 and the drive unit 48 urges the first portion 14 away from the second portion 16 when the motor 46 rotates in the first direction. Conversely, the drive unit 48 urges the first portion 14 toward the second portion 16 when the motor 46 rotates in the second direction. The drive unit 48 may comprise a gear that engages teeth on the respective second rail 44, an electromechanical actuator or any other mechanism that is capable of converting the rotation of the motor 46 into linear movement of the bed frame 12.

A toilet support 50 is coupled to the bed frame 12 and the toilet support 50 is positioned beneath the first portion 14 and the second portion 16. The toilet support 50 comprises a first member 52 that is coupled to the first cross member 34. The first member 52 has a distal end 54 with respect to the first cross member 34 and the distal end 54 of the first member 52 is directed toward the second section of the bed frame 12. The toilet support 50 includes a second member 56 that is coupled to the second cross member 36. The second member 56 has a distal end 58 with respect to the second cross member 36 and the distal end 58 is directed toward the first section of the bed frame 12.

The toilet support 50 includes a panel 60 that has a top surface 62 and a perimeter edge 64, and the perimeter edge 64 has a front side 66 and a back side 68. The distal end 54 of the first member 52 is coupled to the front side 66 of the perimeter edge 64 and the distal end 58 of the second member 56 is coupled to the back side 68 of the perimeter edge 64. The panel 60 is oriented such that the top surface 62 lies on a horizontal plane having the panel 60 being positioned beneath the bottom side 22 of the bed frame 12. Moreover, the panel 60 is aligned with the opening 18 defined between the first portion 14 and the second portion 16 of the bed frame 12 when the bed frame 12 is positioned in the open position.

A portable toilet 70 is provided that is positioned on the toilet support 50. The portable toilet 70 is aligned with the opening 18 between the first portion 14 and the second portion 16 when the bed frame 12 is positioned in the open position. In this way the portable toilet 70 can be employed by the patient 19 while the patient 19 is lying on the bed frame 12. The portable toilet 70 is positioned on the top surface 62 of the panel 60 and the portable toilet 70 may include a water tank, a waste reservoir and other components common the portable toilets. Additionally, a curtain 72 is suspended from the bed frame 12 and the curtain 72 surrounds the portable toilet 70.

A receiver 76 is coupled to the bed frame 12 and the receiver 76 is electrically coupled to the motor 46. The receiver 76 may comprise a radio frequency receiver or the like. A power cord 78 is coupled to and extends away from the bed frame 12 and the power cord 78 is electrically coupled to the motor 46. The power cord 78 has a distal end 80 with respect to the bed frame 12 and a male plug 82 is electrically coupled thereto for plugging into a power source 84 comprising a female electrical outlet.

A remote control 84 is provided and the remote control 84 is positionable on the bed frame 12 such that the remote control 84 is accessible to the patient 19. The remote control 84 is in wireless communication with the motor 46 and the remote control 84 broadcasts an open command to the motor 46 or a close command to the motor 46. The remote control 84 includes a pain button 86 movably integrated into the remote control 84, an open button 88 movably integrated into the remote control 84, a close button 90 movably integrated into the remote control 84 and a call button 92 movably integrated into the remote control 84.

The remote control 84 includes a transmitter 94 that is integrated into the remote control 84. Each of the pain button 86, the open button 88, the close button 90 and the call button 92 is electrically coupled to the transmitter 94. The transmitter 94 is in wireless communication with the receiver 76 and the transmitter 94 may comprise a radio frequency transmitter or the like. The motor 46 is actuated to turn in the first direction when the open button 88 is depressed and the motor 46 is actuated to turn in the second direction when the close button 90 is depressed.

The remote control 84 includes a remote control power supply 96 that is integrated into the remote control 84. The remote control power supply 96 is electrically coupled to the transmitter 94 and the remote control power supply 96 comprises at least one battery. A nurse call 98 is provided that can be carried by a nurse caring for the patient 19 and the nurse call 98 is in wireless communication with the remote control 84. Additionally, the nurse call 98 receives an alert when either the call button 92 is depressed or the pain button 86 is depressed. The nurse call 98 includes a receiver 100 that is in wireless communication with the transmitter 94 in the remote control 84, and the receiver may be a radio frequency receiver or the like.

In use, the patient 19 manipulates the remote control 84 to urge the bed frame 12 into the open position to facilitate the patient 19 to employ the portable toilet 70. In this way the patient 19 can relieve themselves without assistance. The patient 19 manipulates the remote control 84 to urge the bed frame 12 into the closed position when the patient 19 is finished employing the portable toilet 70. Additionally, the patient 19 can call the nurse when the patient 19 is finished employing the portable toilet 70 such that the nurse can empty the portable toilet 70. The patient 19 can additionally call the nurse when the patient 19 is experiencing pain or when the patient 19 needs assistance from the nurse for any reason.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A motorized hospital bed assembly being automatically positionable in a spread position thereby facilitating a patient to employ a bedpan without assistance, said assembly comprising:
    a bed frame comprising a first portion slidably engaging a second portion, said bed frame being positionable in a closed position having said first portion abutting said second portion, said bed frame being positionable in an open position having said first portion being spaced from said second portion to define an opening extending between said first portion and said second portion;
    a first mattress being positioned on said first portion of said bed frame wherein said first mattress is configured to have a patient lie thereon;
    a second mattress being positioned on said second portion of said bed frame wherein said second mattress is configured to have the patient lie thereon, said first mattress abutting said second mattress when said bed frame is positioned in said closed position, said second mattress being spaced from said first mattress when said bed frame is positioned in said open position;
    a motor being coupled to said bed frame, said motor rotating in a first direction or a second direction when said motor is turned on;
    a drive unit being engaged to said motor, said drive unit being engaged to each of said first portion and said second portion, said drive unit urging said first portion away from said second portion when said motor rotates in said first direction, said drive unit urging said first portion toward said second portion when said motor rotates in said second direction;
    a toilet support being coupled to said bed frame, said toilet support being positioned beneath said first portion and said second portion;
    a portable toilet being positioned on said toilet support, said portable toilet being aligned with said opening between said first portion and said second portion when said bed frame is positioned in said open position wherein said portable toilet is configured to be employed by the patient while the patient is lying on said bed frame;
    a remote control being positionable on said bed frame wherein said remote control is configured to be accessible to the patient, said remote control being in wireless communication with said motor, said remote control broadcasting an open command to said motor or a close command to said motor;
    a nurse call being configured to be carried by a nurse caring for the patient, said nurse call being in wireless communication with said remote control, said nurse call receiving an alert when either said call button is depressed or said pain button is depressed, said nurse call including a receiver being in wireless communication with said transmitter in said remote control;
    a pair of first rails, each of said first rails being coupled to and extending away from said first portion of said bed frame; and
    a pair of second rails, each of said second rails being coupled to and extending away from said second portion of said bed frame, each of said second rails slidably engaging a respective one of said first rails thereby slidably attaching said first portion to said second portion.

2. The assembly according to claim 1, wherein said first portion has a length being greater than a length of said second portion wherein said opening is configured to be aligned with the user's lower torso when said bed frame is positioned in said open position, said bed frame having a bottom side and a top side.

3. The assembly according to claim 2, further comprising:
    a plurality of legs, each of said legs being coupled to and extending downwardly from said bed frame, each of said legs having a distal end with respect to said bottom side of said bed frame; and
    a plurality of rollers, each of said rollers being rotatably coupled to said distal end of a respective one of said legs wherein each of said rollers is configured to roll along a support surface thereby supporting said bed frame above the support surface.

4. A motorized hospital bed assembly being automatically positionable in a spread position thereby facilitating a patient to employ a bedpan without assistance, said assembly comprising:
    a bed frame comprising a first portion slidably engaging a second portion, said bed frame being positionable in a closed position having said first portion abutting said second portion, said bed frame being positionable in an open position having said first portion being spaced from said second portion to define an opening extending between said first portion and said second portion;
    a first mattress being positioned on said first portion of said bed frame wherein said first mattress is configured to have a patient lie thereon;
    a second mattress being positioned on said second portion of said bed frame wherein said second mattress is configured to have the patient lie thereon, said first mattress abutting said second mattress when said bed frame is positioned in said closed position, said second mattress being spaced from said first mattress when said bed frame is positioned in said open position;
    a motor being coupled to said bed frame, said motor rotating in a first direction or a second direction when said motor is turned on;
    a drive unit being engaged to said motor, said drive unit being engaged to each of said first portion and said second portion, said drive unit urging said first portion away from said second portion when said motor rotates in said first direction, said drive unit urging said first portion toward said second portion when said motor rotates in said second direction;

a toilet support being coupled to said bed frame, said toilet support being positioned beneath said first portion and said second portion;

a portable toilet being positioned on said toilet support, said portable toilet being aligned with said opening between said first portion and said second portion when said bed frame is positioned in said open position wherein said portable toilet is configured to be employed by the patient while the patient is lying on said bed frame;

a remote control being positionable on said bed frame wherein said remote control is configured to be accessible to the patient, said remote control being in wireless communication with said motor, said remote control broadcasting an open command to said motor or a close command to said motor;

a nurse call being configured to be carried by a nurse caring for the patient, said nurse call being in wireless communication with said remote control, said nurse call receiving an alert when either said call button is depressed or said pain button is depressed, said nurse call including a receiver being in wireless communication with said transmitter in said remote control;

wherein said first portion has a length being greater than a length of said second portion wherein said opening is configured to be aligned with the user's lower torso when said bed frame is positioned in said open position, said bed frame having a bottom side and a top side;

a plurality of legs, each of said legs being coupled to and extending downwardly from said bed frame, each of said legs having a distal end with respect to said bottom side of said bed frame;

a plurality of rollers, each of said rollers being rotatably coupled to said distal end of a respective one of said legs wherein each of said rollers is configured to roll along a support surface thereby supporting said bed frame above the support surface;

a first cross member being coupled between a respective pair of said legs being associated with said first section of said bed frame; and a second cross member being coupled between a respective pair of said legs being associated with said second section of said bed frame.

5. A motorized hospital bed assembly being automatically positionable in a spread position thereby facilitating a patient to employ a bedpan without assistance, said assembly comprising:

a bed frame comprising a first portion slidably engaging a second portion, said bed frame being positionable in a closed position having said first portion abutting said second portion, said bed frame being positionable in an open position having said first portion being spaced from said second portion to define an opening extending between said first portion and said second portion, said first portion having a length being greater than a length of said second portion wherein said opening is configured to be aligned with the user's lower torso when said bed frame is positioned in said open position, said bed frame having a bottom side and a top side;

a plurality of legs, each of said legs being coupled to and extending downwardly from said bed frame, each of said legs having a distal end with respect to said bottom side of said bed frame;

a plurality of rollers, each of said rollers being rotatably coupled to said distal end of a respective one of said legs wherein each of said rollers is configured to roll along a support surfaced thereby supporting said bed frame above the support surface;

a first cross member being coupled between a respective pair of said legs being associated with said first section of said bed frame;

a second cross member being coupled between a respective pair of said legs being associated with said second section of said bed frame;

a first mattress being positioned on said first portion of said bed frame wherein said first mattress is configured to have a patient lie thereon, said first mattress being positioned on said top side of said bed frame;

a second mattress being positioned on said second portion of said bed frame wherein said second mattress is configured to have the patient lie thereon, said first mattress abutting said second mattress when said bed frame is positioned in said closed position, said second mattress being spaced from said first mattress when said bed frame is positioned in said open position, said second mattress being positioned on said top side of said bed frame;

a pair of first rails, each of said first rails being coupled to and extending away from said first portion of said bed frame, each of said first rails being positioned on said bottom side;

a pair of second rails, each of said second rails being coupled to and extending away from said second portion of said bed frame, each of said second rails being positioned on said bottom side, each of said second rails slidably engaging a respective one of said first rails thereby slidably attaching said first portion to said second portion;

a motor being coupled to said bed frame, said motor rotating in a first direction or a second direction when said motor is turned on;

a drive unit being coupled to a respective one of said first rails, said drive unit engaging said second rail that engages said first rail to which said drive unit is coupled, said drive being engaged to said motor, said drive unit urging said first portion away from said second portion when said motor rotates in said first direction, said drive unit urging said first portion toward said second portion when said motor rotates in said second direction;

a toilet support being coupled to said bed frame, said toilet support being positioned beneath said first portion and said second portion, said toilet support comprising:

a first member being coupled to said first cross member, said first member having a distal end with respect to said first cross member, said distal end being directed toward said second section of said bed frame;

a second member being coupled to said second cross member, said second member having a distal end with respect to said second cross member, said distal end being directed toward said first section of said bed frame; and a panel having a top surface and a perimeter edge, said perimeter edge having a front side and a back side, said front side having said distal end of said first member being coupled thereto, said back side having said distal end of said second member being coupled thereto, said panel being oriented such that said top surface lies on a horizontal plane having said panel being positioned beneath said bottom side of said bed frame, said panel being aligned with said opening defined between said first portion and said second portion of said bed frame when said bed frame is positioned in said open position;

a portable toilet being positioned on said toilet support, said portable toilet being aligned with said opening between said first portion and said second portion when said bed frame is positioned in said open position wherein said portable toilet is configured to be employed by the patient while the patient is lying on said bed frame, said portable toilet being positioned on said top surface of said panel;

a curtain being suspended from said bed frame and surrounding said portable toilet;

a receiver being coupled to said bed frame, said receiver being electrically coupled to said motor;

a power cord being coupled to and extending away from said bed frame, said power cord being electrically coupled to said motor, said power cord having a distal end with respect to said bed frame, said distal end having a male plug being electrically coupled thereto wherein said male plug is configured to be plugged into a power source comprising a female electrical outlet;

a remote control being positionable on said bed frame wherein said remote control is configured to be accessible to the patient, said remote control being in wireless communication with said motor, said remote control broadcasting an open command to said motor or a close command to said motor, said remote control including:
  a pain button being movably integrated into said remote control;
  an open button being movably integrated into said remote control;
  a close button being movably integrated into said remote control;
  a call button being movably integrated into said remote control;
  a transmitter being integrated into said remote control, each of said pain button, said open button, said close button and said call button being electrically coupled to said transmitter, said transmitter being in wireless communication with said receiver, said motor being actuated to turn in said first direction when said open button is depressed, said motor being actuated to turn in said second direction when said close button is depressed; and
  a remote control power supply being integrated into said remote control, said remote control power supply being electrically coupled to said transmitter, said remote control power supply comprising at least one battery; and a nurse call being configured to be carried by a nurse caring for the patient, said nurse call being in wireless communication with said remote control, said nurse call receiving an alert when either said call button is depressed or said pain button is depressed, said nurse call including a receiver being in wireless communication with said transmitter in said remote control.

6. A motorized hospital bed assembly being automatically positionable in a spread position thereby facilitating a patient to employ a bedpan without assistance, said assembly comprising:

a bed frame comprising a first portion slidably engaging a second portion, said bed frame being positionable in a closed position having said first portion abutting said second portion, said bed frame being positionable in an open position having said first portion being spaced from said second portion to define an opening extending between said first portion and said second portion;

a first mattress being positioned on said first portion of said bed frame wherein said first mattress is configured to have a patient lie thereon;

a second mattress being positioned on said second portion of said bed frame wherein said second mattress is configured to have the patient lie thereon, said first mattress abutting said second mattress when said bed frame is positioned in said closed position, said second mattress being spaced from said first mattress when said bed frame is positioned in said open position;

a motor being coupled to said bed frame, said motor rotating in a first direction or a second direction when said motor is turned on;

a drive unit being engaged to said motor, said drive unit being engaged to each of said first portion and said second portion, said drive unit urging said first portion away from said second portion when said motor rotates in said first direction, said drive unit urging said first portion toward said second portion when said motor rotates in said second direction;

a toilet support being coupled to said bed frame, said toilet support being positioned beneath said first portion and said second portion;

a portable toilet being positioned on said toilet support, said portable toilet being aligned with said opening between said first portion and said second portion when said bed frame is positioned in said open position wherein said portable toilet is configured to be employed by the patient while the patient is lying on said bed frame;

a remote control being positionable on said bed frame wherein said remote control is configured to be accessible to the patient, said remote control being in wireless communication with said motor, said remote control broadcasting an open command to said motor or a close command to said motor;

a nurse call being configured to be carried by a nurse caring for the patient, said nurse call being in wireless communication with said remote control, said nurse call receiving an alert when either said call button is depressed or said pain button is depressed, said nurse call including a receiver being in wireless communication with said transmitter in said remote control; and wherein said toilet support comprising:
  a first member being coupled to said first cross member, said first member having a distal end with respect to said first cross member, said distal end being directed toward said second section of said bed frame; and
  a second member being coupled to said second cross member, said second member having a distal end with respect to said second cross member, said distal end being directed toward said first section of said bed frame.

7. The assembly according to claim 6, wherein said toilet support includes a panel having a top surface and a perimeter edge, said perimeter edge having a front side and a back side, said front side having said distal end of said first member being coupled thereto, said back side having said distal end of said second member being coupled thereto, said panel being oriented such that said top surface lies on a horizontal plane having said panel being positioned beneath said bottom side of said bed frame, said panel being aligned with said opening defined between said first portion and said second portion of said bed frame when said bed frame is positioned in said open position.

8. A motorized hospital bed assembly being automatically positionable in a spread position thereby facilitating a patient to employ a bedpan without assistance, said assembly comprising:

a bed frame comprising a first portion slidably engaging a second portion, said bed frame being positionable in a closed position having said first portion abutting said second portion, said bed frame being positionable in an open position having said first portion being spaced from said second portion to define an opening extending between said first portion and said second portion;

a first mattress being positioned on said first portion of said bed frame wherein said first mattress is configured to have a patient lie thereon;

a second mattress being positioned on said second portion of said bed frame wherein said second mattress is configured to have the patient lie thereon, said first mattress abutting said second mattress when said bed frame is positioned in said closed position, said second mattress being spaced from said first mattress when said bed frame is positioned in said open position;

a motor being coupled to said bed frame, said motor rotating in a first direction or a second direction when said motor is turned on;

a drive unit being engaged to said motor, said drive unit being engaged to each of said first portion and said second portion, said drive unit urging said first portion away from said second portion when said motor rotates in said first direction, said drive unit urging said first portion toward said second portion when said motor rotates in said second direction;

a toilet support being coupled to said bed frame, said toilet support being positioned beneath said first portion and said second portion;

a portable toilet being positioned on said toilet support, said portable toilet being aligned with said opening between said first portion and said second portion when said bed frame is positioned in said open position wherein said portable toilet is configured to be employed by the patient while the patient is lying on said bed frame;

a remote control being positionable on said bed frame wherein said remote control is configured to be accessible to the patient, said remote control being in wireless communication with said motor, said remote control broadcasting an open command to said motor or a close command to said motor;

a nurse call being configured to be carried by a nurse caring for the patient, said nurse call being in wireless communication with said remote control, said nurse call receiving an alert when either said call button is depressed or said pain button is depressed, said nurse call including a receiver being in wireless communication with said transmitter in said remote control;

wherein said remote control includes:
   a pain button being movably integrated into said remote control;
   an open button being movably integrated into said remote control;
   a close button being movably integrated into said remote control; and
   a call button being movably integrated into said remote control.

9. The assembly according to claim 8, further comprising:
   a receiver being coupled to said bed frame, said receiver being electrically coupled to said motor; and
   a transmitter being integrated into said remote control, each of said pain button, said open button, said close button and said call button being electrically coupled to said transmitter, said transmitter being in wireless communication with said receiver, said motor being actuated to turn in said first direction when said open button is depressed, said motor being actuated to turn in said second direction when said close button is depressed.

\* \* \* \* \*